United States Patent [19]

Eden

[11] Patent Number: 5,340,747

[45] Date of Patent: Aug. 23, 1994

[54] DIAGNOSTIC MICROBIOLOGICAL TESTING APPARATUS AND METHOD

[75] Inventor: Gideon Eden, Ann Arbor, Mich.

[73] Assignee: Difco Laboratories, Inc., Ann Arbor, Mich.

[21] Appl. No.: 72,346

[22] Filed: Jun. 4, 1993

[51] Int. Cl.$^5$ .................... C12M 1/34; G01N 21/64; G01N 21/76; G01N 35/02

[52] U.S. Cl. .................... 436/172; 250/361 C; 250/461.2; 422/52; 422/58; 422/64; 422/82.08; 422/82.09; 435/291; 435/808; 435/809; 436/45; 436/46; 436/807

[58] Field of Search ............... 435/29, 289, 291, 808, 435/809; 422/52, 58, 63, 64, 67, 82.08, 82.09; 436/46, 45, 172, 800, 807; 250/361 C, 461.2, 328; 356/417

[56] References Cited

U.S. PATENT DOCUMENTS

| | | | |
|---|---|---|---|
| 3,297,873 | 1/1967 | Hovnanian et al. | 356/416 |
| 4,061,469 | 12/1977 | DuBose | 422/64 |
| 4,166,095 | 8/1979 | Kling et al. | 422/67 |
| 4,175,860 | 11/1979 | Bacus | 356/39 |
| 4,400,353 | 8/1983 | Meserol et al. | 422/73 |
| 4,431,307 | 2/1984 | Suovaniemi | 356/246 |
| 4,453,266 | 6/1984 | Bacus | 382/6 |
| 4,580,895 | 4/1986 | Patel | 356/39 |
| 4,695,727 | 9/1987 | Brierley et al. | 250/328 |
| 4,720,463 | 1/1988 | Farber et al. | 435/291 |
| 4,784,947 | 11/1988 | Noeller | 435/291 |
| 4,856,073 | 8/1989 | Farber et al. | 422/67 |
| 4,940,332 | 7/1990 | Miwa et al. | 435/291 |
| 4,956,148 | 9/1990 | Grandone | 422/63 |
| 5,064,756 | 11/1991 | Carr et al. | 436/172 |
| 5,096,807 | 3/1992 | Leaback | 422/52 |
| 5,112,736 | 5/1992 | Caldwell et al. | 435/291 |
| 5,162,654 | 11/1992 | Kostichka et al. | 250/461.2 |

*Primary Examiner*—Robert J. Warden
*Assistant Examiner*—L. M. Crawford
*Attorney, Agent, or Firm*—Reising, Ethington, Barnard, Perry & Milton

[57] ABSTRACT

A diagnostic microbiological testing apparatus and method includes at least one test tray including a plurality of reaction chambers, a light source disposed proximate to the test tray for directing light, at an excitation wavelength of a fluorescence emitting agent contained within the reaction chambers, at the test tray, a filter for passing therethrough only light generated by a fluorescence emitting reaction resulting from the interaction of the fluorescence emitting agent and a sample, and an imaging mechanism for detecting only the light generated by the fluorescence emitting reaction at the emission wavelength simultaneously from the plurality of reaction chambers.

5 Claims, 2 Drawing Sheets

DIAGNOSTIC MICROBIOLOGICAL TESTING APPARATUS AND METHOD

This is a continuation-in-part of Ser. No. 07/848,087 filed on Mar. 9, 1992, now abandoned.

TECHNICAL FIELD

The present invention relates to microbiological testing apparatus and methods and, more specifically, to means for susceptibility and identification testing of samples, such as those from patients possibly infected by a microbe.

BACKGROUND OF THE INVENTION

Many systems exist for conducting tests of microbiological samples for providing patient diagnosis and therapy. It is desirable to use automated systems requiring minimal handling by a technician. At the same time, it is also desirable to utilize systems which provide the most accurate results possible.

Such systems as described above can be used for identification testing wherein it is desirable to determine the identification of any microbes present in a patient's sample. Alternatively, or additionally, it is also desirable to utilize a systems which can be used for susceptibility testing. Susceptibility testing determines the susceptibility of a microbe in a sample to various therapeutics, such as antibiotics.

The U.S. Pat. No. 3,297,873 to Hovnanian discloses a television camera utilized with a control unit in video amplifier, a horizontal line analyzer and a TV monitor. This provides a visual read-out of micro-organisms. The TV monitor displays the specimen or a part of the specimen utilizing a lens and filter combination. Furthermore, a photometer determines the UV absorption or transmission characteristics of micro-organisms, cells or other micro-specimens. The display includes a darkened area, as well as a display of area. The darkened area represents the micro-sampled portion of the specimen.

The U.S. Pat. No. 4,061,469 to DuBose discloses a blood analyzer which utilizes two photodetectors, one as the measuring detector of the sample and the other as a reference detector. The second photodetector senses energy supplied from the source through an individual sample.

The U.S. Pat. No. 4,166,095 to Kling discloses an automatic chemical testing apparatus with visual monitoring and inputting of test results.

The U.S. Pat. No. 4,175,860 to Bacus discloses a method and apparatus for classifying cells, such as red blood cells. The apparatus generates an image that is split into a high resolution and a low resolution image wherein the circuitry performs measurement and analysis relating to the size, density and color of the cytoplasm and the nucleus. The analysis obtained from each of the two images are applied to classification logic circuitry for the purpose of determining malignant cells. The images are obtained from a ridicom camera which are sent to an analog digital converter and to a video monitor. A single slide is used.

The U.S. Pat. No. 4,431,307 to Suovaniemi discloses a particular type of cuvette whose slide walls are provided with a layer of material that prevent measurement of radiation or light directed at the walls for passing through the side walls. The patent discloses that a photo-measurement will be taken of each individual cuvette and the material therein.

The U.S. Pat. No. 4,400,353 to Meseral, etal. discloses an electro-optical system for use in evaluating immunological reactions. Fluid biological test specimens and a reagent are introduced into a reaction zone in an image cell. The reaction cells are formed of two planar surfaces made of glass or plastic material which are provided with a generally circular groove to define the reaction cell. A fill port is pierced in a circular groove for introducing the reagent and the biological fluid. Each image cell is lifted out of its respective compartment and brought into the optical pass sequentially. After transluminating the reaction zone and imaging light being transmitted therethrough on an image sensor, the dark areas formed on the surface of the image sensor are measured by electronics. The image sensor is a charge coupled device (CCD). When several indicator particles agglutinate, the resulting image will shadow several pixels which appear darker than a single particle. The CCD is scanned electronically row by row to obtain each pixel of information. The image areas are quantified electronically and the total area is obtained which is a function of the concentration of the antibody in the wells. The total dark images of the control specimen is related to the respective concentrations. The imaged data is fed to a threshold comparator and particle counter which screens the non-agglutinated particles on the basis of both intensity and particle size.

The U.S. Pat. No. 4,453,266 to Bacus discloses a method and apparatus for measuring cell volume of a red blood cell on a slide. The apparatus includes means for generating signals representative of the area of the cells, and means for measuring the optical density of the individual cells and for generating signals representative of the hemoglobin or massive cells. More than one red blood cell is determined. The image is obtained by a television camera which sends this image to electronics for the analysis. Each of the several cells displayed in the image are independently analyzed.

The U.S. Pat. No. 4,580,895 to Patel discloses a scanning photometer for reading agglutination tests and other procedures by scanning the contents of a microtest well or other sample holding vessel to determine certain characteristics of the content. The patent discloses scanning an entire tray having a plurality of wells and obtaining a video image across each well. The tray or plate which is utilized has an array of uniformly diametered, upwardly opening sample-holding wells. An XY mover is connected to the holder to move the sensor assembly in a horizontal X-Y coordinate plane to successively bring wells in a preselected order to axial alignment with photodetector. The sensor assembly comprises a photo beam interrupt comb which has a set of parallel and uniformly spaced apart photo beam interrupting teeth arranged in a straight row extending parallel to the motion path of the carriage in X coordinate axis. The assembly also comprises a photo beam interrupt comb which has eight parallel teeth which extend in the Y coordinate axis. The combs cause the production of interrupt signals to the microprocessor to aid in the movement of the tray and designation of each well. The scanning operation is repeated column for column of each of the columns in plate. The photodetector's analog output signal is a measurement of the intensity of the photometers light beam and represents a continuous, traveling measurement of the optical density of the substance in diametrically across each entire well and the optical density of the well bottom.

Twenty-four signal samples of the photodetector analog output are digitized periodically such that samples are uniformly spaced apart diametrically across each well. The digital optical density readings of each of the wells are processed by the microcomputer. The photodetector obtains a sample across a diameter of the wells, rather than the entire circle of the well. The microcomputer utilizes a threshold value in a determination of lights and darks of the sample.

The U.S. Pat. No. 4,784,947 to Noeller discloses still photographing a plurality of samples at a single time.

The U.S. Pat. Nos. 4,720,463 and 4,856,073, both to Farber et al. relate to an apparatus and process of automatically obtaining test results from microbiological test rays. In general, microbiological sample and agent to be tested are placed in test rays having a plurality of wells or cupolas. The trays are moved to an incubator for a predetermined time. Thereafter, the trays are moved to an inspection station. A light source is disposed above the tray and a pair of video cameras are disposed below the tray in the inspection station. The video cameras take images of the tray, well by well, and a processor processes the images to analyze the test results. The processor records the background light level of each point or pixel only within the area of interest for each particular well of the tray. For each well, the image processor determines the number of pixels in the area of interest which have an associated voltage exceeding a predetermined threshold for that area of interest. If the number of pixels exceeds a predetermined number, a positive result is assigned to that well. The image processor analyzes the binary partial results from the wells to determine possible identity of the micro-organisms.

The present invention provides a drastic simplification of the prior art apparatus which more accurately identifies and provides a susceptibility testing of a sample. The present invention utilizes a mechanically simple system which utilizes a fluorescent reaction for our identification and susceptibility testing. The fluorescent determinations are faster and much more accurate than prior art determinations due to the high signal to noise ratio of fluorometric systems. Further, an entire tray including a plurality of wells can be imaged simultaneously, not requiring a well by well video inspection. This will increase the speed of inspection, which will provide adequate time for "real time" detection, identification and susceptability analysis.

SUMMARY OF THE INVENTION

In accordance with the present invention, there is provided a diagnostic microbiological testing apparatus for detecting the presence of a fluorescence emitting reaction (FER) resulting from the interaction of fluorescence emitting agents (FEA) and a sample for detection, susceptibility, and identification testing, the apparatus including a test tray including a plurality of reaction chambers containing the FEA, which upon reaction with a predetermined microbe in the sample will emit light at a predetermined emission wavelength upon being illuminated by light at a predetermined excitation wavelength. A light source is disposed proximate to the test tray for directing light, at the excitation wavelength, at the reaction chamber. Filter means passes therethrough only light generated by the FER at the emission wavelength. Video means detects only the light generated by the FER at the emission wavelength simultaneously from the plurality of reaction chambers, the filter means being disposed between the test tray and the video means.

The present invention further provides a method of detecting the presence of the FER resulting from the interaction of the FEA and a sample for detection, susceptibility, and identification testing by containing the FEA in the plurality of reaction chambers, directing light at the excitation wavelength at the chambers, passing through a filter only light generated by the FER at the emission wavelength, and video imaging only the passed through light generated by the FER at the emission wavelength simultaneously from the plurality of reaction chambers.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

A diagnostic microbiological testing apparatus instructed in accordance with the present invention is generally shown at 10 in the Figures. The apparatus is specifically useful for detecting the presence of a fluorescence emitting reaction (FER) resulting from the interaction of fluorescence emitting agents (FEA) and a sample for detection, susceptibility and identification testing.

Many FEA have been characterized for use in detection, susceptibility and identification testing. The U.S. Pat. No. 5,164,301 to Thomson, issued Nov. 17, 1992 and assigned to the assignee of the present invention discloses a two-dye technology for detecting, identifying and susceptibility testing of samples. The technology includes a metabolic dye which changes in response to such environmental factors as pH or enzymatic cleavage, and an analytical dye. Examples of such FEA are medias containing metabolic dyes such as resazurin, indoxyl and chloroindoyl compounds and analytical dyes such as sulforhodamine, rhodamine B, eosin V and flourescein. Examples of such media are simple media chosen to promote the growth of microorganisms tested. The media may contain carbohydrates. It may be made to grow specific microbes or a broad spectrum of microbes. Such media are well known in the art, such as Mueller-Hinton, Columbian broth, Schaedler's broth, Brain heart broth, and tryptic soy broth.

Samples to be tested in accordance with the present invention and utilizing the apparatus made in accordance with the present invention can be various solid or fluid samples taken from a patient. The samples can be in the form of blood samples, plasma samples, spinal fluid samples or the like. Of course, the present invention could be used for veterinary and other purposes.

Figure 2:
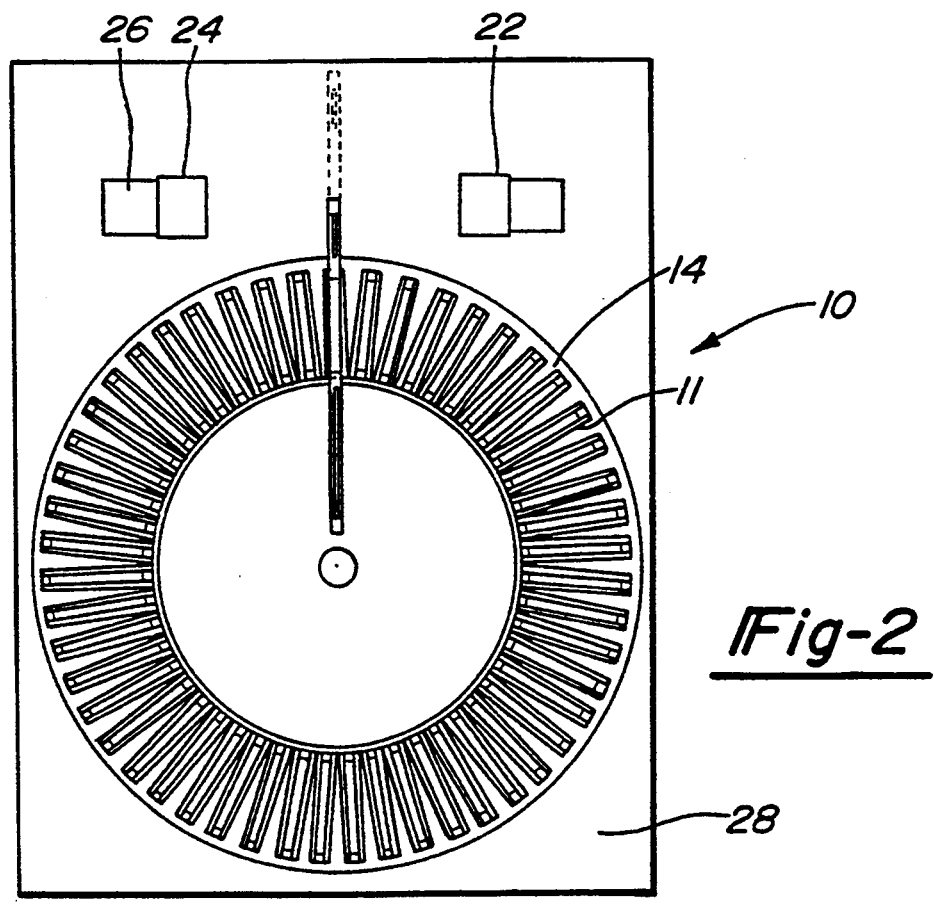
FIG. 2 is a top plan view taken substantially along lines 2—2 of FIG. 1.
Figure 3:
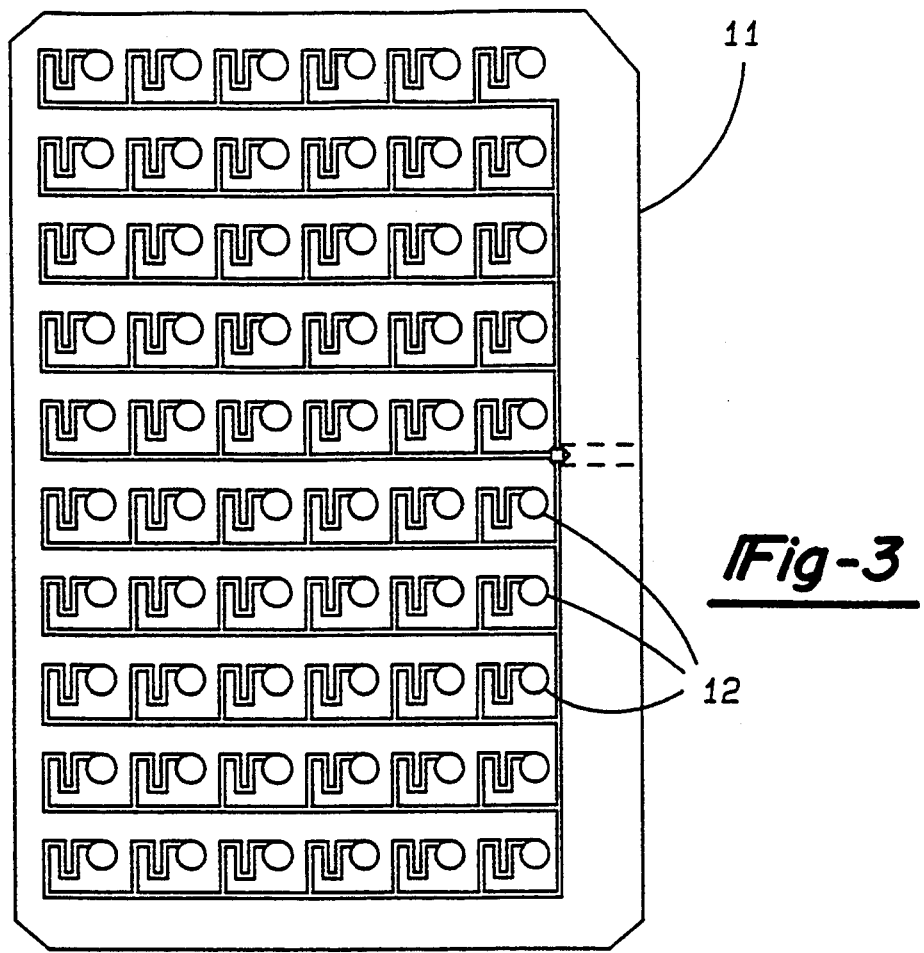
FIG. 3 is a plan view of a test tray for use with the present invention.

Generally, the apparatus 10 includes a plurality of reaction chambers in the form of test tray 11. As shown in FIG. 2, the apparatus 10 can include a plurality of test trays 11 contained within a carousel 14 which is effectively a rotary table rotated by an actuating and indexing mechanism 16. The carousel 14 is rotated to be able to index one of the test trays 11 proximate to a detection area 18, as shown in FIG. 2. Positioning means 20, such as a reciprocating arm mechanism, positions one of the test trays 11, proximate to the detection area 18, into and out of the detection area for purposes as explained below. That is, the carousel 14 would allow in and out sliding movement of a test tray 11 as actuated by the positioning mechanism 20 into and out of the detection area 18.

A light source, schematically shown at 22 in FIG. 2, is disposed proximate to the test tray 11 disposed in the detection area 18. The light source 22 is a high energy narrow band light source which can excite fluorogenic agents at specific bands such as, gas filled electron discharge tubes or lasers. The light source provides a high energy narrow band wavelength light sufficient to produce an emission fluorescence in the presence of a microbe in the sample to be detectable by the video mechanism 26, as discussed below. A filter 24 is shown to be disposed on the side of the test tray 11 opposite to the light source 22. The filter 24 is of the type that passes therethrough only light generated by the FER at the emission wavelength. That is, the filter 24 filters out light at all other wavelengths than the emission wavelength from passing therethrough. Thusly, the only light detectable beyond the filter 24 is light generated by the FER. All other images, such as an image of the test tray 11, are not detectable beyond the filter 24. Further, all of the reaction chambers 12 are detectable if an FER is present therein. Otherwise, even the reaction chamber 12 is not detectable as it will emit no detectable light beyond the filter 24.

The apparatus 10 includes a video mechanism 26, the filter 24 being disposed between the video mechanism 26 and test tray 11. Moreover, the only light detectable by the video mechanism 26 is the light which passes through to the filter 24. Thusly, the video mechanism 26 is only exposed to light generated by the FER at the emission wavelength. By using the filter 24, a video mechanism (two-dimensional optical detector) such as a diode array or CCD device can be used which receives, detects, and produces an image from a broad spectrum of wavelengths but the filter 24 will only expose the video mechanism 26 to the light emitted by the FER at the emission wavelength. The narrow band light source provides sufficient energy so that the light passing through the filter 24 is of sufficient magnitude so as to be detectable by the CCD device. Thusly, the video mechanism 26 will detect only the light emitted by the FER and will not image any other objects illuminated by the light source 22, such as the reaction chamber 12. Further, the video mechanism 26 will image all FER simultaneously when the test tray 11 is disposed at the detection area 18. Thusly, a series of reaction chambers 12 can be imaged, unlike prior art systems which must scan each reaction chamber separately.

The above components of the apparatus 10 are contained within a body portion 28, having a lid member 30. The body portion 28 and lid 30 completely isolate outside light sources from the detecting system comprising the light source 22, test tray 11, filter 24 and video mechanism 26.

Figure 1:
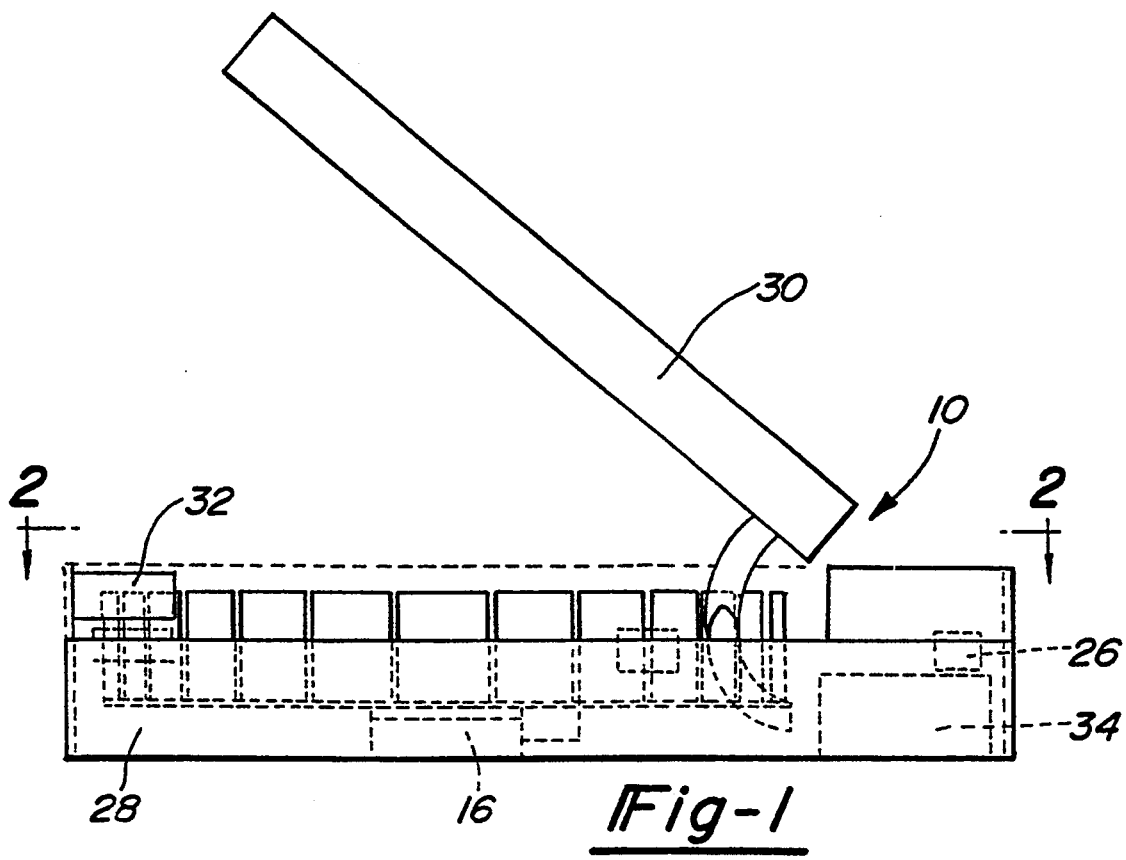
FIG. 1 is an elevational view of an apparatus made in accordance with the present invention.

Since the reactions occurring in the test trays 11 need to be controlled with regard to temperature, the apparatus 10 can include a temperature control and display schematically shown at 32 in FIG. 1. The apparatus also includes control electronics schematically shown at 34 for controlling the operation of the carousel 14, camera 26 and positioning mechanism 16.

The present invention further provides a method of detecting the presence of the FER resulting from the interaction of the FEA and the sample for detection, susceptibility and identification testing. Specifically, the method includes the steps of containing the FEA in a plurality of reaction chambers 12, the FEA upon reaction with a predetermined microbe in a sample contained within the reaction chamber 12 emitting light at the predetermined emission wavelength upon being illuminated by light at the predetermined excitation wavelength. Light is directed at the excitation wavelength from the light source 22 to the reaction chambers 12. A filter 24 passes therethrough only light generated by the FER at the emission wavelength and the passed through light generated by the FER at the emission wavelength from the plurality of reaction chambers 12 is simultaneously detected by the video mechanism 26.

Figure 4:
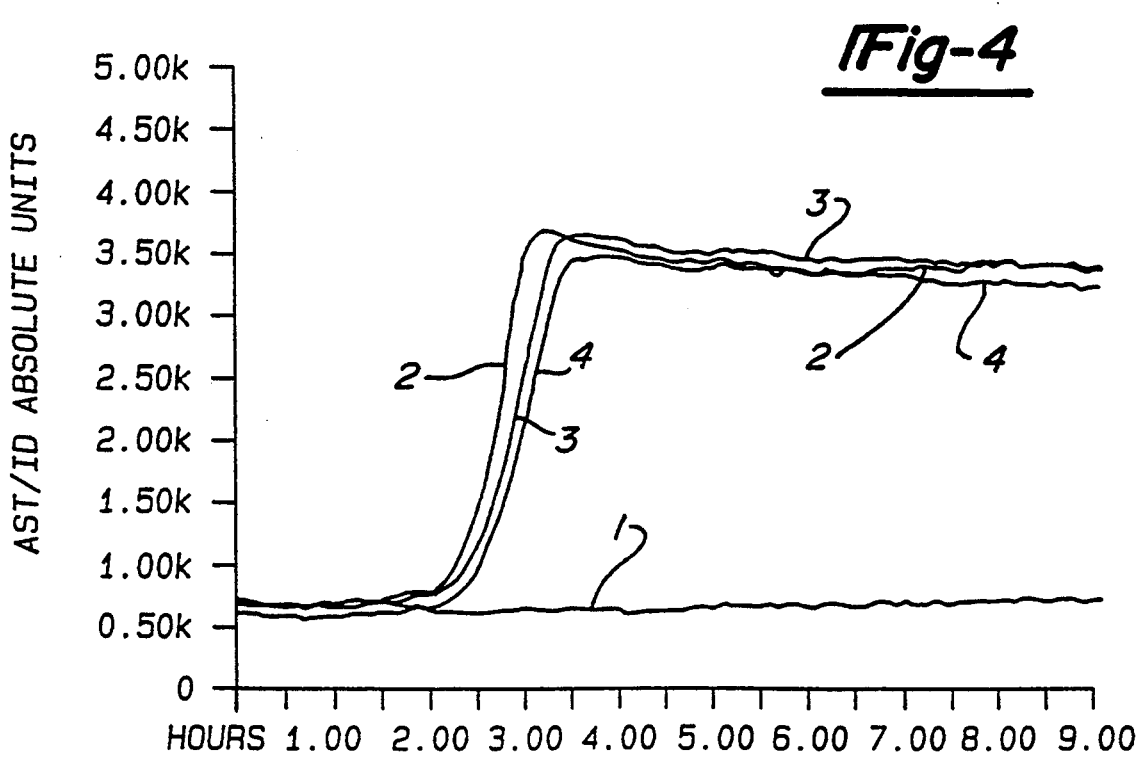
FIG. 4 is an example of susceptability testing used in accordance with the present invention.

The following example demonstrates the ability of the present invention to perform susceptibility testing. The inoculum which is comprised of: growth media (Mueller Hinton base at 22 g/L), fluorogenic substance (sulforhodamine 101 at 10 $\mu$M), reaction dye (resazurin at 20 $\mu$M), antimicrobial agent (Aztreonam at various concentrations) and *Providencia alcalifaciens* at $5 \times 10^5$ cfu/m$\iota$, is introduced to multiple reaction chambers with the capacity of 50 $\mu\iota$ each. The test plate is incubated by setting the carousel temperature to 35° C., and amplitude readings are taken every 6 minutes. FIG. 4 illustrates the time curves of the various samples in which curves #2, 3 and 4 indicate growth of microorganisms due to the low concentration of antibiotics (neg. control, 4, 8 $\mu$g/m$\iota$.) in the corresponding chambers. Curve #1 shows the growth inhibition of the microorganisms in the presence of the higher antibiotic concentration (the Minimal Inhibition Concentration - MIC) of 16 units.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A diagnostic microbiological testing apparatus for detecting the presence of fluorescence emitting reaction (FER) resulting from the interaction of fluorescence emitting agents (FEA) and a sample for susceptibility and identification testing, said apparatus consisting essentially of: a test tray including a plurality of reaction chambers containing an FEA, which upon reaction with a predetermined microbe in a sample will emit light at a predetermined emission wavelength upon being illuminated by light at a predetermined excitation wavelength;

a narrow band light source disposed proximate to said plurality of reaction chambers of said test tray for directing light substantially at said excitation wavelength at said plurality of reaction chambers;

filter means for passing therethrough only light generated by the FER at the emission wavelength; and
a video means for detecting only the light generated by an FER at the emission wavelength simultaneously from all the said plurality of reaction chambers of said test tray and forming an image thereof, said filter means being disposed between said test tray and video means.

2. An apparatus as set forth in claim 1 further including a detection area, carousel means for containing a plurality of said test trays, indexing means for sequentially moving said carousel to selectively position each of said test trays proximate to said detection area, and positioning means for positioning one of said test trays proximate to said detection area into and out of said detection area.

3. An apparatus as set forth in claim 1 further including reaction media for reacting with a predetermined microbe to emit the light at said emission wavelength, said video means detecting the presence of the microbe by detecting said light at said emission wavelength.

4. An apparatus as set forth in claim 1 wherein said reaction chambers further include an antibiotic for susceptibility testing.

5. A method of detecting the presence of a fluorescence emitting reaction (FER) resulting from the interaction of fluorescence emitting agents (FEA) and a sample for susceptibility and identification testing, said method consisting essentially of the steps of: containing an FEA in a plurality of reaction chambers of a test tray, the FEA upon reaction with a predetermined microbe in a sample emitting light at a predetermined emission wavelength upon being illuminated by light at a predetermined excitation wavelength;

directing a narrow band light substantially at the excitation wavelength at the plurality of reaction chambers of the test tray passing through a filter only light generated by an FER at the emission wavelength simultaneously from the plurality of reaction chambers; and video imaging only the passed through light generated by the FER at the emission wavelength simultaneously from all of the plurality of reaction chambers of the test tray.

* * * * *